United States Patent [19]
Rock et al.

[11] Patent Number: 6,162,942
[45] Date of Patent: Dec. 19, 2000

[54] METHOD FOR PRODUCING AROMATIC NITRILES

[75] Inventors: Michael-Harold Rock, Valby, Denmark; Albrecht Marhold, Leverkusen, Germany

[73] Assignee: Bayer Aktiengesellschaft, Leverkusen, Germany

[21] Appl. No.: 09/367,752

[22] PCT Filed: Feb. 9, 1998

[86] PCT No.: PCT/EP98/00696

§ 371 Date: Aug. 17, 1999

§ 102(e) Date: Aug. 17, 1999

[87] PCT Pub. No.: WO98/37058

PCT Pub. Date: Aug. 27, 1998

[30] Foreign Application Priority Data

Feb. 20, 1997 [DE] Germany .......................... 197 06 648

[51] Int. Cl.$^7$ ................................. C07C 253/00
[52] U.S. Cl. ........................ 558/337; 558/338; 558/343
[58] Field of Search ................................. 558/337, 338, 558/343

[56] References Cited

FOREIGN PATENT DOCUMENTS

| | | |
|---|---|---|
| 2010159 | 8/1990 | Canada . |
| 0 384 392 | 8/1990 | European Pat. Off. . |
| 0 613 719 | 9/1994 | European Pat. Off. . |
| 0 613 720 | 9/1994 | European Pat. Off. . |
| 96/11906 | 4/1996 | WIPO . |

OTHER PUBLICATIONS

Adv. in Chem. Series 132: Homogeneous Catalysis II, pp. 252–273 (month unavailable) 1974.
Bull. Chem. Soc. of Japan, 61, pp. 9185–1990, Jun. 1988.
Journal of Organometallic Chemistry, pp. 335–339 (month unavailable) 1979.
Chem. Abstracts, vol. 82, No. 13, Mar. 31, 1975, Abstract No. 85632.
Chem. Abstracts, vol. 125, No. 5, Jul. 29, 1996, Abstract No. 58095.

*Primary Examiner*—Cecilia Tsang
*Assistant Examiner*—Joseph Murray
*Attorney, Agent, or Firm*—Joseph C. Gil; Diderico van Eyl

[57] ABSTRACT

A process for preparing aromatic nitriles from corresponding chloroaromatics by reaction with cyanides.

10 Claims, No Drawings

METHOD FOR PRODUCING AROMATIC NITRILES

This application is a 371 of PCT/EP98/00696 filed Feb. 9, 1998.

FIELD OF THE INVENTION

The present invention relates to a process for preparing aromatic nitriles from corresponding chloroaromatics by reaction with cyanides. Substituted benzonitriles and other aromatic nitriles are intermediates which are frequently employed in the preparation of pharmaceutical and agricultural active compounds.

BACKGROUND OF THE INVENTION

It is known that aryl halides can be converted into aromatic nitrites using alkali metal cyanides in the presence of catalysts, for example nickel complexes. Adv. in Chem. Series 132: Homogeneous Catalysis II, 252–273 (1974) describes the nickel-catalysed cyanation of aryl halides with alkali metal cyanides in detail. The catalysts used were Ni(0) or Ni(II) complexes having generally mono- or bidentate arylphosphine ligands. The solvents used were alcohols, such as methanol and ethanol, and dipolar-aprotic solvents, such as dimethylformamide. It is only possible to carry out the reaction with good yields if the concentration of the cyanide ions is controlled exactly. Acetone has been employed as solvent only for the cyanation of unsubstituted chlorobenzene. Here, a selectivity of 82% was achieved, at a conversion of 58%, and 10% of an undesired coupling product (biphenyl) were obtained. For a process that is to be carried out on an industrial scale, these are very unfavourable values. Later, it was found that the catalyst is cyanated irreversibly at higher cyanide concentrations see Bull. Chem. Soc. Jpn. 61, 1985 (1988) and J. Organomet. Chem. 173, 335 (1979)).

EP-A 384 392 describes the cyanation of optionally halogen-, formyl- or trifluoro-methyl-substituted chloro- or bromobenzene in the presence of catalysts prepared in situ from nickel chloride. The reaction is carried out in anhydrous lower alcohols or dipolar aprotic solvents. Here, the yields are frequently unsatisfactory. In many cases, a further disadvantage is dehalogenation, which proceeds as a side reaction. The preferred solvent—acetonitrile owing to its toxicity and tetrahydrofuran owing to its tendency to form peroxides—can be handled on an industrial scale only with great expense.

For 2-thio-3-amino-chlorobenzene, WO 96/11906 describes the cyanation in the presence of phosphine nickel catalysts in aprotic polar solvents. Not to mention the specific substitution pattern of the substrate, the 11–22 mol % of tetrakis-triphenylphosphine-nickel constitute uneconomically high amounts of catalyst. EP-A 613 720 likewise describes a process for preparing aromatic nitriles in which the preferred solvent employed is tetrahydrofuran, which has the above-mentioned disadvantages.

SUMMARY OF THE INVENTION

This invention, accordingly, provides a process for preparing aromatic nitriles of the formula

 (I), in which
Ar represents substituted phenyl or substituted naphthyl or optionally substituted biphenyl, optionally substituted phenyl which contains a fused-on 3- to 5-membered heterocycle, or represents hetaryl which contains 5 to 10 ring members and is optionally substituted, possible substituents being up to five identical or different substituents selected from the group consisting of $C_1$–$C_{12}$-alkyl, $C_1$–$C_{12}$-halogenoalkyl, $C_1$–$C_{12}$-alkoxy, $C_1$–$C_{12}$halogenoalkoxy, $C_1$–$C_6$-alkylsulphonyl, $C_1$–$C_6$-halogenoalkylsulphonyl, $C_1$–$C_{12}$-alkylcarbonyl, $C_1$–$C_{12}$-alkoxycarbonyl, fluorine, formyl, nitro and cyano, where the $C_1$–$C_{12}$-alkyl for its part may be substituted by 1 to 4 $C_1$–$C_6$-alkoxy groups,
by reacting chloroaromatics of the formula

 (II), in which
Ar is as defined under formula (I) in the presence of nickel(0) and/or nickel (II) complexes with potassium cyanide and/or sodium cyanide, characterized in that the process is carried out in the presence of an optionally cyclic ketone having at least four carbon atoms.

DESCRIPTION OF THE INVENTION

Ketones to be employed according to the invention have, compared with the dipolar aprotic solvents which have hitherto been used, the advantage of lower toxicity and higher stability towards atmospheric oxygen. Compared with acetone, when using the process according to the invention for the cyanation of unsubstituted chlorobenzene, better selectivities are achieved at higher conversions, and in each case, considerably less undesired coupling products are formed. Consequently, the process according to the invention can be carried out more simply on an industrial scale and is more effective than known processes for preparing aromatic nitriles.

In halogenoalkyl, halogenoalkoxy and halogenoalkylsulphonyl, halogen represents, for example, fluorine, chlorine or bromine. Halogenoalkyl, halogenoalkoxy and halogenoalkylsulphonyl may be halogenated by one, by more than one or completely with halogen atoms.

In the case of phenyl with a fused-on 3- to 5-membered heterocycle, the fused-on hetero moiety can contain, for example, from 1 to 3 atoms selected from the group consisting of nitrogen and oxygen. Examples include: benzo-1,3-dioxolyls, in particular 2,2-difluorobenzo-1,3-dioxol-5-yl, benzo-1,4-dioxinyls, in particular 2,2,3,3-tetrafluorobenzo-1,4-dioxinyl, benzofuryl, 2,3-dihydrobenzofuryl, indolyl and 2,3-dihydroindolyl.

Hetaryl which contains 5 to 10 ring members can, for example, contain from 1 to 4 atoms selected from the group consisting of nitrogen and oxygen in the ring, with a maximum of 2 oxygen atoms being present.

Examples include pyridyl, pyrimidyl, purinyl, furyl and oxazolyl.

Ar preferably represents substituted phenyl or substituted naphthyl or optionally substituted biphenyl, optionally substituted phenyl which contains a fused-on 3- to 5-membered heterocycle, or represents hetaryl which contains 5 to 10 ring members and is optionally substituted, possible substituents being up to 4 identical or different substituents selected from the group consisting of $C_1$–$C_8$-alkyl, $C_1$–$C_8$-fluoroalkyl having up to 10 fluorine atoms, $C_1$–$C_8$-chloroalkyl having up to 10 chlorine atoms, fluorochloroalkyl having 1 to 8 carbon atoms and a total of up to 10 fluorine and chlorine atoms, $C_1$–$C_8$-alkoxy, $C_1$–$C_8$-fluoroalkoxy having up to 10 fluorine atoms, $C_1$–$C_8$-chloroalkoxy having up to 10 chlorine atoms, $C_1$–$C_8$-fluorochloroalkoxy having a total of up to 10 fluorine and chlorine atoms, $C_1$–$C_4$-alkylsulphonyl, $C_1$–$C_4$-fluoroalkylsulphonyl having up to 5 fluorine atoms, $C_1$–$C_4$-chloroalkylsulphonyl having up to 5 chlorine atoms, fluorochloroalkylsulphonyl having up to 1 to 4 carbon atoms and a total of up to 5 fluorine and chlorine atoms, $C_1$–$C_4$-alkylcarbonyl, $C_1$–$C_4$-alkoxycarbonyl, fluorine, formyl, nitro or cyano, where the $C_1$–$C_8$-alkyl for its part may be substituted by 1 to 3 $C_1$–$C_4$-alkoxy groups.

Ar particularly preferably represents phenyl which is substituted by 1 to 3 fluorine atoms, 1 to 2 $C_1$–$C_2$-fluoroalkyl groups, 1 to 2 $C_1$–$C_2$-fluoroalkoxy groups, 1 to 2 $C_1$–$C_2$-fluoroalkylsulphonyl groups or 1 to 2 formyl groups and optionally additionally by 1 to 2 $C_1$–$C_4$-alkyl groups.

Optionally cyclic ketones to be employed according to the invention are preferably those having 4 to 13 carbon atoms. Examples include: methyl ethyl ketone, methyl isobutyl ketone, diethyl ketone, cyclopentanone, cyclohexanone and dicyclohexyl ketone. Particular preference is given to methyl ethyl ketone. Expediently, the ketone is chosen such that its boiling point differs by at least 20° C. from that of the nitrile of the formula (I) formed.

Ketones to be employed according to the invention can be used in amounts of, for example, from 50 to 2000 ml, preferably from 100 to 500 ml, in each case based on 1 mol of chloroaromatic.

Suitable nickel (0) and nickel(II) complexes are, for example, catalytically active compounds of the formula (III)

$$\text{NiL}^1\text{L}^2\text{L}^3_n\text{L}^4_m \quad (III),$$

in which either
i) n and m independently of one another in each case represent zero or 1 and
$L^1$, $L^2$, $L^3$ and $L^4$ independently of one another represent phosphine ligands $PQ_3$ in which
Q independently of one another in each case represents $C_1$–$C_8$-alkyl, $C_3$–$C_8$-cycloalkyl, optionally $C_1$–$C_8$-alkyl-, $C_1$–$C_4$-hydroxyalkyl-, $C_1$–$C_6$-alkoxy-, di-$C_1$–$C_4$-alkylamino-$C_1$–$C_4$-alkyl-, fluorine-, hydroxysulphonyl- or di-$C_1$–$C_4$-alkylamino-substituted phenyl, or
$L^1$ and $L^2$ and/or $L^3$ and $L^4$ in each case together represent bidentate phosphine ligands $Q_2P$—W—$PQ_2$ in which W represents $C_1$–$C_8$-alkylene or ferrocenyl which is optionally monosubstituted by one of the substituents listed above for Q=phenyl, and
Q is as defined above or in which
ii) n and m each represent 1 and
$L^1$ and $L^2$ together represent a bidentate phosphine ligand $Q^1Q^2P$—$W^1$—$PQ^3Q^4$ in which
$Q^1$, $Q^2$, $Q^3$ and $Q^4$ independently of one another represent halogen-, $C_1$–$C_4$-alkyl-, $C_1$–$C_4$-halogenoalkyl-, cyano-, amino-, $C_1$–$C_4$-alkyl-amino-, di-$C_1$–$C_4$-alkyl-amino-, $C_1$–$C_4$-alkoxy- or $C_1$–$C_4$-alkylthio-substituted phenyl or hetaryl containing 5 to 10 ring members and N, O and/or S atoms,
$W^1$ represents a metallocene biradical, $C_3$–$C_8$-alkylene or the group —$Ar^1$—$(R)_p$—$Ar^1$— where
$Ar^1$ represents phenyl or hetaryl containing 5 to 10 ring members and N, O and/or S atoms,
p represents zero or 1 and
R represents $C_1$–$C_8$-alkylene which is optionally interrupted by 1 to 3 heteroatoms selected from the series consisting of oxygen and sulphur, $L^3$ represents $C_1$–$C_4$-alkyl or represents phenyl, phenylcarbonyl, phenoxy, phenoxycarbonyl or phenyl-$C_1$–$C_4$-alkyl each of which is optionally mono- to penta-substituted independently of one another by $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy, halogen, cyano, formyl, $C_1$–$C_8$-alkylcarbonyl, $C_1$–$C_8$-alkoxycarbonyl, and
$L^4$ represents chlorine, bromine, iodine, $C_1$–$C_4$-alkyl or optionally $C_1$–$C_4$-alkyl-substituted aryl or hetaryl which contains 5 to 10 ring members and N, O and/or S atom, or
$L^3$ and $L^4$ together represent a diene $R^1$—CH—$(CH_2)_q$—CH=CH—$R^2$ in which
q represents 1, 2, 3 or 4 and
$R^1$ and $R^2$ in each case independently of one another represent $C_1$–$C_4$-alkyl or together represent $C_1$–$C_4$-alkylene.

If $W^1$ denotes a metallocene biradical, preference is given to ferrocene.

In the definitions for the formula (III), aryl represents, for example, phenyl or naphthyl, and heteroaryl represents, for example, thienyl, pyridyl, furyl, pyrrolyl, N-($C_1$–$C_4$-alkyl)-pyrrolyl or thiazolyl.

Tris-triphenylphosphine-nickel is a particularly suitable nickel compound of the formula (III).

The preparation of nickel compounds suitable for carrying out the process according to the invention is described, for example, in WO 96/11906, EP-A 613 720, EP-A 384 392, and in the literature cited therein.

For example, from 0.95 to 1.5 mol, preferably from 1.0 to 1.2 mol, of sodium cyanide and/or potassium cyanide and from 0.001 to 0.1 mol, preferably from 0.005 to 0.1 mol, of nickel complexes can be employed in the process according to the invention, in each case per mole of chloroaromatic of the formula (II).

The reaction is carried out, for example, at from 40 to 120° C., preferably at from 50 to 100° C.

The process according to the invention is usually carried out under atmospheric pressure. It is also possible to operate under reduced or elevated pressure.

In an advantageous variant of the process according to the invention, nickel(0) complexes are employed which are prepared in the solvent to be used according to the invention from a nickel(II) precursor by reduction with, for example, base metals, such as magnesium, zinc or manganese, if appropriate in the presence of an excess of a complex ligand, only immediately prior to the cyanation.

In a particularly preferred variant, bis-triphenylphosphine-nickel dichloride is initially prepared from anhydrous nickel dichloride and triphenylphosphine in anhydrous dimethylformamide. Distillative removal of the solvent under reduced pressure then gives the anhydrous nickel(II) complex which is used for the reaction in the solvent according to the invention. Addition of activated zinc powder and triphenylphosphine gives the activated nickel catalyst. The chloroaromatic is then added and the mixture is then stirred and, after addition of the alkali metal cyanide, heated.

Work-up of the reaction mixture which is present after the reaction can be carried out, for example, by removing the solid components by filtration, washing the filter cake with an organic solvent, for example the ketone employed according to the invention, combining the organic phases and working them up distillatively.

It is surprising that, when ketones having at least four carbon atoms are employed, the reaction proceeds with good yields, since the cyanation of chlorobenzene with potassium cyanide in acetone works relatively poorly (see above). Moreover, if the ketones are employed according to the invention at the same catalyst concentration and reaction time, a considerably higher conversion is frequently obtained. Finally, the formation of undesirable coupling products of the biphenyl type is substantially lower.

The invention is further described in the following illustrative examples in which all parts and percentages are by weight unless otherwise indicated.

EXAMPLES

Example 1

Preparation of bis-triphenylphosphine-nickel dichloride (catalyst precursor)

A mixture of 30.1 g of low-water nickel dichloride (0.31% by weight of water according to Karl-Fischer) and 122.5 g of triphenylphosphine in 200 ml of dimethylformamide (DMF) were boiled at reflux under an atmosphere of nitrogen for 90 minutes. The solvent was then distilled off under reduced pressure. This gave 172.2 g of $NiCl_2(PPh_3)_2$ as an air-stable but moisture-sensitive solid which contained 19.6 g of DMF. Further concentration gave 156.5 g of a green, virtually DMF-free solid which was likewise air-stable but moisture-sensitive.

Both products (DMF-containing and DMF-free) can be employed successfully as precursor for the in-situ-preparation of a catalyst of the composition $Ni(PPh_3)_3$. When the DMF-free product was used, an approximately 10% higher conversion of the chloroaromatics of the formula (II) was observed.

Example 2

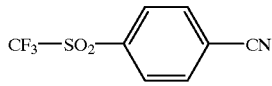

Preparation of 4-trifluoromethanesulphonylbenzonitrile a) Process According to the Invention in Methyl Ethyl Ketone (MEK)

Under an atmosphere of nitrogen, a mixture of 4 g of bis-triphenylphosphine-nickel dichloride, 3 g of triphenylphosphine and 100 ml of MEK was stirred at room temperature for 10 minutes. 1.2 g of activated zinc powder were then added, and the reaction mixture was stirred at 70° C. for 30 minutes. Following this, the mixture was allowed to cool to 25° C., and a solution of 92 g of 4-chloro-trifluoromethanesulphonylbenzene in 50 ml of MEK was added dropwise. The mixture was stirred for 10 minutes, 18.5 g of sodium cyanide were then added and the reaction mixture was stirred at from 65 to 70° C. for 20 h. The conversion after this period of time was greater than 98% (GC). After cooling to RT, the mixture was filtered, the solid filter residue was washed 2× with 30 ml of MEK each time and the combined organic phases were concentrated under reduced pressure. Fractionation under reduced pressure via a 30 cm Vigreux column and heated distillation bridge gave 76 g (85% of theory) of 4-trifluoromethanesulphonylbenzonitrile as a white solid (boiling point at 0.2 mbar: 115° C.). A formation of coupling products was not observed.

b) Process According to the Invention in Methyl Isobutyl Ketone (MIBK)

The method of a) was repeated using 110 g of 4-chlorotrifluoromethanesulphonylbenzene in 150 ml of MIBK, giving 62.1 g (59% of theory) of 4-trifluoromethanesulphonylbenzonitrile. The conversion after 20 h was approximately 71% (GC). A formation of coupling products was not observed.

c) Comparative Example

Method a) was repeated, but using the same volume of DMF instead of MFK. After 20 h, gas chromatography showed a conversion of only 15% to the desired 4-trifluoromethanesulphonylbenzonitrile.

Example 3

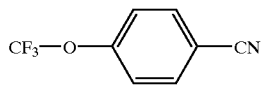

Preparation of 4-trifluoromethoxybenzonitrile a) Process According to the Invention in MEK Under an atmosphere of nitrogen, a mixture of 6.5 g of bis-triphenylphosphine-nickel dichloride, 5 g of triphenylphosphine and 120 ml of MEK was stirred at room temperature for 10 minutes. 1.9 g of activated zinc powder were then added, and the reaction mixture was stirred at 70° C. for 30 minutes. Following this, the mixture was allowed to cool to 25° C., and 93.25 g of 1-chloro-4-trifluoromethoxybenzene were added dropwise. The mixture was stirred for 10 minutes, 24 g of sodium cyanide were added, and the reaction mixture was stirred at from 65 to 70° C. for 20 h. The conversion was then approximately 75% (GC). After cooling to room temperature, the mixture was filtered, the solid filter residue was washed 2× with 50 ml of MEK and the combined organic phases were concentrated under reduced pressure. Vacuum distillation gave 58.5 g (66% of theory) of 4-trifluoromethoxybenzonitrile as a colourless liquid (boiling point at 120 mbar: 80° C.). 2.6% of coupling products had formed.

b) Comparative Example

Method a) was repeated, but the same volume of acetonitrile was used instead of MEK. After the same reaction time, a conversion of only approximately 35% had been reached (GC). Work-up gave 29 g (32.5% of theory) of trifluoromethoxybenzonitrile.

Example 4

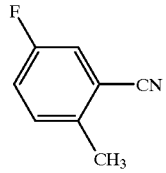

Preparation of 5-fluoro-2-methylbenzonitrile a) Process According to the Invention in MEK By the method of Example 3, 72.5 g of 2-chloro-4-fluorotoluene in 100 ml of MEK gave 46.7 g (68% of theory)

of 5-fluoro-2-methylbenzonitrile (boiling point at 30 mbar: 110° C.). After 20 h, the conversion was approximately 80% (GC). 1.2% of coupling products had formed.

b) Comparative Example

Method a) was repeated, but the same volume of tetrahydrofuran was used instead of MEK. After the same reaction time, a conversion of only approximately 44% had been reached. Work-up gave 26.1 g (38% of theory) of 5-fluoro-2-methylbenzonitrile.

Example 5

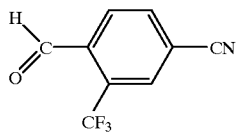

Preparation of 4-cyano-2-trifluoromethylbenzaldehyde

By the method of Example 3, 68 g of 4-chloro-2-trifluoromethylbenzaldehyde in 100 ml of diethyl ketone gave, after short-path distillation, 41.2 g (63.4% of theory) of 4-cyano-2-trifluoromethylbenzaldehyde as a colourless solid (boiling point at 0.5 mbar: 95° C.). After 20 h, the conversion was almost complete (96%, GC). 5% of coupling products had formed.

Example 6

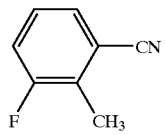

Preparation of 3-fluoro-2-methylbenzonitrile

By the method of Example 3, 72.25 g of 2-chloro-6-fluorotoluene in 100 ml of cyclohexanone gave 46.2 g (68.5% of theory) of 3-fluoro-2-methylbenzonitrile (boiling point at 50 mbar: 104° C.). After 20 h, the conversion was approximately 90% (GC). 2% of coupling products had formed.

Example 7

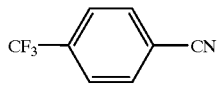

Preparation of 4-trifluoromethylbenzonitrile

By the method of Example 3, 180.5 g of 4-chlorobenzotrifluoride in 200 ml of MEK gave, after fractionation via a 30 cm Vigreux column and heated distillation bridge, 136.6 g (79% of theory) of 4-trifluoromethylbenzonitrile as a colourless solid. 2.2% of coupling products had formed.

Example 8

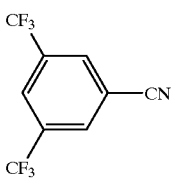

Preparation of 3,5-bis-(trifluoromethyl)-benzonitrile

By the method of Example 3, 124 g of 1-chloro-3,5-bis-(trifluoromethyl)-benzene in 120 ml of ethyl methyl ketone gave 61.4 g (51.2% of theory) of 3,5-bis-(trifluoromethyl)-benzonitrile (b.p.$_{.45\ mbar}$: 88° C.). After 20 hours, the conversion was approximately 60%. 4.5% of coupling products had formed.

Example 9

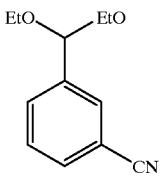

Preparation of 3-diethoxymethyl-benzonitrile

By the method of Example 3a), 107.25 g of 3-chloro-diethoxymethyl-benzene in 100 ml of MEK gave 83.3 g (81.2% of theory) of 3-diethoxymethyl-benzonitrile (boiling point at 0.5 bar: 110° C.). After 4 hours, the conversion was 95%.

Although the present invention has been described in detail with reference to certain preferred versions thereof, other variations are possible. Therefore, the spirit and scope of the appended claims should not be limited to the description of the versions contained therein.

What is claimed is:

1. Process for preparing aromatic nitriles of the formula $$Ar\text{—}CN \qquad (I),$$

in which

Ar represents substituted phenyl or substituted naphthyl or optionally substituted biphenyl, optionally substituted phenyl which contains a fused-on 3- to 5-membered heterocycle, or represents hetaryl which contains 5 to 10 ring members and is optionally substituted, possible substituents being up to five identical or different substituents selected from the group consisting of $C_1$–$C_{12}$-alkyl, $C_1$–$C_{12}$-halogenoalkyl, $C_1$–$C_{12}$-alkoxy, $C_1$–$C_{12}$-halogenoalkoxy, $C_1$–$C_6$-alkylsulphonyl, $C_1$–$C_6$-halogenoalkylsulphonyl, $C_1$–$C_{12}$-alkylcarbonyl, $C_1$–$C_{12}$-alkoxycarbonyl, fluorine, formyl, nitro and cyano, where the $C_1$–$C_{12}$-alkyl for its part may be substituted by 1 to 4 $C_1$–$C_6$-alkoxy groups, by reacting chloroaromatics of the formula $$Ar\text{—}Cl \qquad (II),$$

in which

Ar is as defined under formula (I) in the presence of nickel(0) and/or nickel (II) complexes with potassium cyanide and/or sodium cyanide, characterized in that the process is carried out in the presence of an optionally cyclic ketone having at least four carbon atoms.

2. Process according to claim 1, characterized in that in the formulae

Ar represents substituted phenyl or substituted naphthyl or optionally substituted biphenyl, optionally substituted phenyl which contains a fused-on 3- to 5-membered heterocycle, or represents hetaryl which contains 5 to 10 ring members and is optionally substituted, possible substituents being up to 4 identical or different substituents selected from the group consisting of $C_1$–$C_8$-alkyl, $C_1$–$C_8$-fluoroalkyl having up to 10 fluorine atoms, $C_1$–$C_8$-chloroalkyl having up to 10 chlorine atoms, fluorochloroalkyl having 1 to 8 carbon atoms and a total of up to 10 fluorine and chlorine atoms, $C_1$–$C_8$-alkoxy, $C_1$–$C_8$-fluoroalkoxy having up to 10 fluorine atoms, $C_1$–$C_8$-chloroalkoxy having up to 10 chlorine atoms, $C_1$–$C_8$-fluorochloroalkoxy having a total of up to 10 fluorine and chlorine atoms, $C_1$–$C_4$-alkylsulphonyl, $C_1$–$C_4$-fluoroalkylsulphonyl having up to 5 fluorine atoms, $C_1$–$C_4$-chloroalkylsulphonyl having up to 5 chlorine atoms, fluorochloroalkylsulphonyl having up to 1 to 4 carbon atoms and a total of up to 5 fluorine and chlorine atoms, $C_1$–$C_4$-alkylcarbonyl, $C_1$–$C_4$-alkoxycarbonyl, fluorine, formyl, nitro or cyano, where the $C_1$–$C_8$-alkyl for its part may be substituted by 1 to 3 $C_1$–$C_4$-alkoxy groups.

3. Process according to claim 1, characterized in that in the formulae

Ar represents phenyl which is substituted by at least 1 to 3 fluorine atoms, 1 to 2 $C_1$–$C_2$-fluoroalkyl groups, 1 to 2 $C_1$–$C_2$-fluoroalkoxy groups, 1 to 2 $C_1$–$C_2$-fluoroalkylsulphonyl groups or 1 to 2 formyl groups and optionally additionally by 1 to 2 $C_1$–$C_4$-alkyl groups.

4. Process according to claim 1, characterized in that the optionally cyclic ketones contain 4 to 13 carbon atoms.

5. Process according to claim 1, characterized in that the ketone is selected from the group consisting of methyl ethyl ketone, methyl isobutyl ketone, diethyl ketone, cyclopentanone, cyclohexanone and dicyclohexyl ketone.

6. Process according to claim 1, characterized in that the nickel(0) and/or nickel(II) complexes used are catalytically active compounds of the formula (III)

$$NiL^1L^2L^3_nL^4_m \qquad (III),$$

in which either i) n and m independently of one another in each case represent zero or 1 and
   $L^1$, $L^2$, $L^3$ and $L^4$ independently of one another represent phosphine ligands $PQ_3$ in which
   Q independently of one another in each case represents $C_1$–$C_8$-alkyl, $C_3$–$C_8$-cycloalkyl, optionally $C_1$–$C_8$-alkyl-, $C_1$–$C_4$-hydroxyalkyl-, $C_1$–$C_6$-alkoxy-, di-$C_1$–$C_4$-alkylamino-$C_1$–$C_4$-alkyl-, fluorine-, hydroxysulphonyl- or di-$C_1$–$C_4$-alkylamino-substituted phenyl, or $L^1$ and $L^2$ and/or $L^3$ and $L^4$ in each case together represent bidentate phosphine ligands $Q_2P$—W—$PQ_2$ in which
   W represents $C_1$–$C_8$-alkylene or ferrocenyl which is optionally monosubstituted by one of the substituents listed above for Q=phenyl, and
   Q is as defined above or in which ii) n and m each represent 1 and
   $L^1$ and $L^2$ together represent a bidentate phosphine ligand $Q^1Q^2P$—$W^1$—$PQ^3Q^4$ in which
   $Q^1$, $Q^2$, $Q^3$ and $Q^4$ independently of one another represent halogen-, $C_1$–$C_4$-alkyl-, $C_1$–$C_4$-halogenoalkyl-, cyano-, amino-, $C_1$–$C_4$-alkylamino-, di-$C_1$–$C_4$-alkyl-amino-, $C_1$–$C_4$-alkoxy- or $C_1$–$C_4$-alkylthio-substituted phenyl or hetaryl containing 5 to 10 ring members and N, O and/or S atoms,
   $W^1$ represents a metallocene biradical, $C_3$–$C_8$-alkylene or the group —$Ar^1$—$(R)_p$—$Ar^1$— where
   $Ar^1$ represents phenyl or hetaryl containing 5 to 10 ring members and N, O and/or S atoms,
   p represents zero or 1 and
   R represents $C_1$–$C_8$-alkylene which is optionally interrupted by 1 to 3 heteroatoms selected from the series consisting of oxygen and sulphur,
   $L^3$ represents $C_1$–$C_4$-alkyl or represents phenyl, phenylcarbonyl, phenoxy, phenoxycarbonyl or phenyl-$C_1$–$C_4$-alkyl each of which is optionally mono- to pentasubstituted independently of one another by $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy, halogen, cyano, formyl, $C_1$–$C_8$-alkylcarbonyl, $C_1$–$C_8$-alkoxycarbonyl, and
   $L^4$ represents chlorine, bromine, iodine, $C_1$–$C_4$-alkyl or optionally $C_1$–$C_4$-alkyl-substituted aryl or hetaryl which contains 5 to 10 ring members and N, O and/or S atom, or
   $L^3$ and $L^4$ together represent a diene $R^1$—CH—$(CH_2)_q$—CH=CH—$R^2$ in which
   q represents 1, 2, 3 or 4 and
   $R^1$ and $R^2$ in each case independently of one another represent a $C_1$–$C_4$-alkyl or together represent $C_1$–$C_4$-alkylene.

7. Process according to claim 1, characterized in that from 0.95 to 1.5 mol of sodium cyanide and/or potassium cyanide and from 0.001 to 0.1 mol of nickel complexes are employed, in each case per mole of chloroaromatic of the formula (II).

8. Process according to claim 1, characterized in that it is carried out at from 40 to 120° C.

9. Process according to claim 1, characterized in that nickel(0) complexes are employed which are prepared in the solvent to be used from a nickel(II) precursor by reduction only immediately prior to the cyanation.

10. Process according to claim 1, characterized in that the reaction mixture which is present after the reaction is worked up by filtering off the solid components, washing the filter cake with an organic solvent, combining the organic phases and working them up distillatively.

* * * * *